United States Patent [19]

Hulse et al.

[11] Patent Number: 5,334,942
[45] Date of Patent: Aug. 2, 1994

[54] METHOD OF, AND DEVICE FOR USE IN MONITORING LEAF WETNESS BY CONDUCTIVITY/RESISTIVITY MESUREMENT

[75] Inventors: Mark M. Hulse, Fayette; W. Hal Shaffer, Jr., Columbia, both of Mo.

[73] Assignee: The Curators of the University of Missouri of Columbia, Missouri, Columbia, Mo.

[21] Appl. No.: 984,339

[22] Filed: Dec. 2, 1992

[51] Int. Cl.$^5$ .................. G01R 27/02; G01N 27/04
[52] U.S. Cl. ..................... 324/694; 324/692; 324/696; 324/724; 340/602; 73/73
[58] Field of Search ............ 324/691, 694, 696, 722, 324/724, 693, 439, 692; 73/73; 340/602, 604

[56] References Cited

U.S. PATENT DOCUMENTS

| | | | |
|---|---|---|---|
| 2,906,952 | 9/1959 | Horecky | 324/694 |
| 2,975,361 | 3/1961 | Holaday | 324/694 |
| 3,264,558 | 8/1966 | Heeps | 324/694 |
| 3,321,726 | 5/1967 | Babylon | 338/34 |
| 3,354,388 | 11/1967 | Perry | 324/694 |
| 3,440,396 | 4/1969 | Greene | 340/602 |
| 3,844,832 | 10/1974 | Gabrusenok | 427/553 |
| 4,023,206 | 5/1977 | Nishibe et al. | 360/75 |
| 4,122,389 | 10/1978 | Haagen | 324/694 |
| 4,345,301 | 8/1982 | Nelson | 361/400 |
| 4,380,169 | 4/1983 | Graham | 73/73 |

OTHER PUBLICATIONS

"Monitoring System Cuts Costs of Crop Spraying", *Columbia Missourian*, Nov. 19, 1986, 1D.
"'Farmer Friendly' Computers Head Off Orchard Disaster", *Missouri Farm News Service*, Oct. 29, 1986, vol. 83, No. 43.
"Resistant Breeds: Apples Armored Against Pests", *The Grower*, Feb. 1989, 10–17.
"Putting Pest Predictors to Work", *The Grower*, Feb. 1988, 10–16.
"Computer Alerts Fruit Growers", *Hannibal Courier–Post*, Nov. 28, 1986.
"Help for Farms from Satellites", *The Maneater*, Oct. 24, 1986.
"Future of Farming Comes to Sanborn", *Ag Columns*, Dec. 1986.
Article from *Missouri Ruralist*, Nov. 1986.

*Primary Examiner*—Gerard R. Strecker
*Assistant Examiner*—Diep Do
*Attorney, Agent, or Firm*—Armstrong, Teasdale, Schlafly & Davis

[57] ABSTRACT

A device for providing a signal emulating the wetness of plant leaves, includes a first generally horizontal surface; a second, generally upwardly facing sloped surface having an edge spaced above the first surface by a gap, so that drops of moisture can accumulate on the second surface, and run off the edge, bridging the gap, and first and second leads extending from the first and second surfaces, respectively, to measure the conductivity/resistivity across the gap. Also disclosed is a method of providing a signal emulating the wetness of plant leaves including the steps of: providing a first generally horizontal surface; providing a second, generally upwardly facing sloped surface having an edge spaced above the first surface by a gap, so that drops of moisture can accumulate on the second surface, and run off the edge, bridging the gap between the first and second surfaces; and measuring the conductivity/resistivity across the gap between the first and second surfaces.

6 Claims, 1 Drawing Sheet

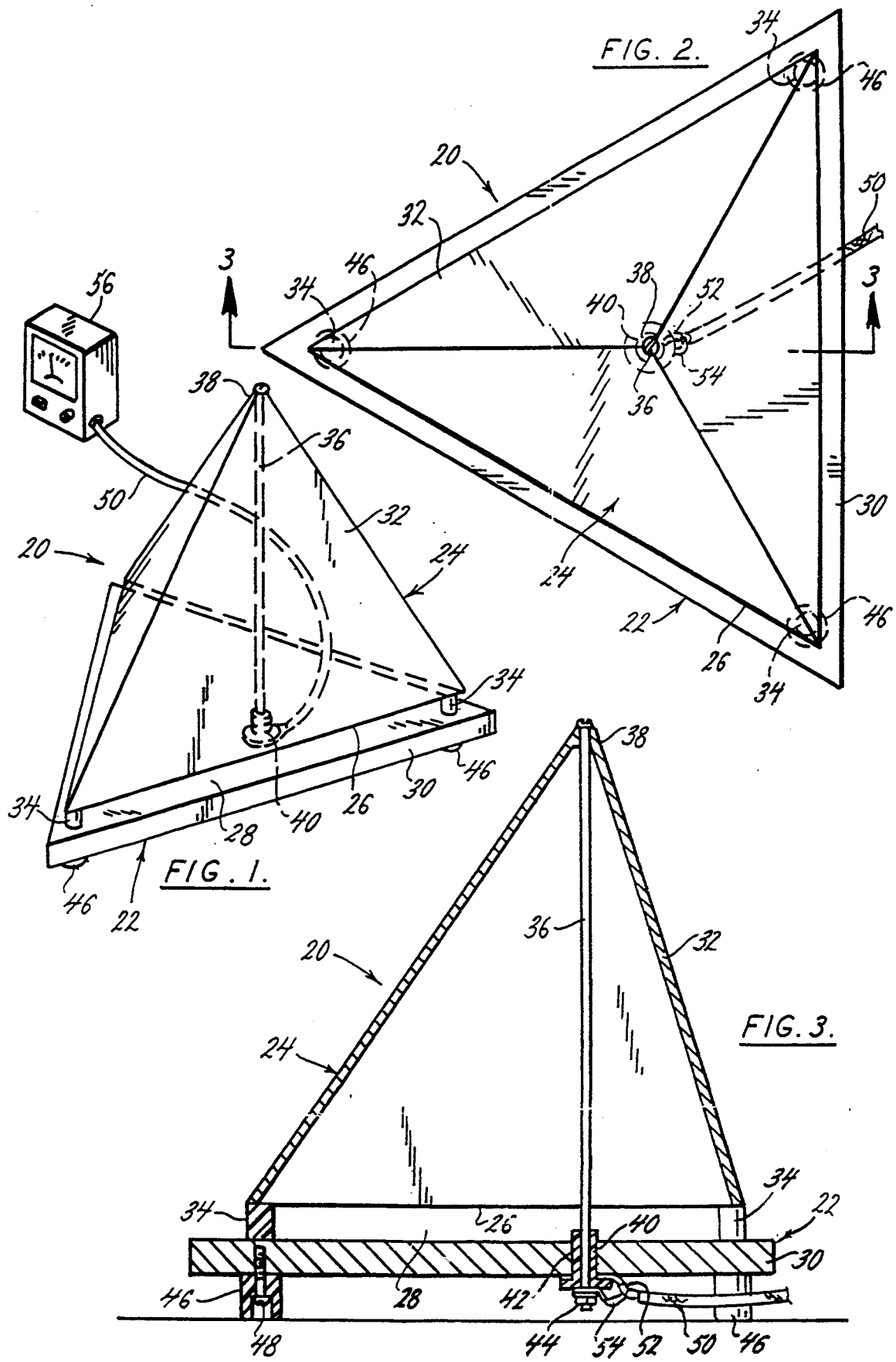

મethOD OF, AND DEVICE FOR USE IN
MONITORING LEAF WETNESS BY
CONDUCTIVITY/RESISTIVITY MESUREMENT

BACKGROUND OF THE INVENTION

This invention relates to a leaf wetness emulator, that is, a device that provides a model of the wetness of plant leaves.

Various types of leaf wetness emulators have been developed to provide a model of the wetness of plant leaves in a particular environment or locale. These emulators are used, for example, to provide input signals for computer programs for plant disease forecasting and for crop management.

One type of leaf wetness emulator involves clip electrodes secured to plant leaves. While this type of emulator has improved accuracy and correlation to actual leaf surface wetness, the electrodes were easily dislodged from the leaves. Moreover, the electrodes tended to pull the leaves on which they were placed from the plants. Examples of other types of prior leaf wetness emulators include a bifilar coil whose windings can be bridged by sufficiently large water droplets, which changes the coil's electrical properties; and a network of parallel conductors printed on a flat epoxy glass substrate, in which adjacent conductors can be bridged by sufficiently large water droplets, which changes the network's electrical properties. It has generally been difficult to correlate these types of prior emulators with the wetness of leaf surfaces in the surrounding environment. Thus these types of emulators can be unreliable.

Thus, the art has lacked a leaf wetness emulator that can reliably provide a signal that accurately correlates to leaf wetness, without need for physical connection to plant leaves.

SUMMARY OF THE INVENTION

The leaf wetness emulator of the present invention provides a signal emulating the wetness of plant leaves. Generally, the device comprises a first generally horizontal surface, and a second, generally upwardly facing sloped surface having an edge spaced above the first surface by a gap. First and second leads extend from the first and second surfaces, respectively to measure the conductivity/resistivity across the gap. Moisture can accumulate and form droplets on the sloped second surface. When the droplets become sufficiently large, they can run off the edge, bridging the gap between the surfaces. When water droplets are present across the gap they increase the conductivity (and decrease the resistivity) across the gap.

In the preferred embodiment, the first surface is generally a polygon, and the second surface is a pyramid with a corresponding polygonal base, positioned over the first surface. Of course the first and second surfaces could have different configurations, for example the first surface could be circular, and the second surface could be conical or frustoconical.

The sensitivity of the emulator, and its ability to correlate to the wetness of particular plant leaves in a particular environment, can be adjusted by varying the surface area of the second surface, by varying the slope of the second surface, by varying the linear length of the edge of the second surface that overlaps the first surface, and by varying the size (height) of the gap between the first and second surfaces. These variables are empirically chosen so that the presence of water droplets bridging the gap correlates to a particular degree of leaf wetness, in a particular environment. Thus, the emulator of the present invention accurately emulates the wetness of plant leaves in a particular locale. These and other features and advantages of the invention will be in part apparent and in part pointed out hereinafter.

BRIEF DESCRIPTION OF THE DRAWINGS

FIG. 1 is a perspective view of a leaf wetness emulator constructed according to the principles of this invention;

FIG. 2 is a top plan view of the leaf wetness emulator; and

FIG. 3 is a vertical cross-sectional view of the leaf wetness emulator taken along the plane of line 3—3 in FIG. 2.

Corresponding reference numerals indicate corresponding parts throughout the several views of the drawings.

DETAILED DESCRIPTION OF THE PREFERRED EMBODIMENT

A leaf wetness emulator constructed according to the principles of this invention is indicated generally as 20 in FIGS. 1-3. The leaf wetness emulator 20 is adapted to provide a signal emulating the wetness of plant leaves. The emulator 20 comprises a first generally horizontal surface 22 and a second, generally upwardly facing sloped surface 24 having an edge 26 spaced above the first surface 22 by a gap 28.

In this preferred embodiment, the first surface 22 comprises a generally triangular plate 30. The plate 30 is preferably made of aluminum, but could be made of some other conductive material. For example, the plate 30 could be a ¼ inch thick, equilateral triangular plate measuring about 3½ inches on each side. The second surface 24 comprises the surface of a pyramid 32. The pyramid 32 is also preferably made of aluminum, but could be made of some other conductive material. For example, each side of the board of the pyramid 32 could have a length of about 3 inches, and the pyramid could have a height of about 2½ inches.

There are spacers 34 at the corners of the pyramid 32 forming the gap 28 between the triangular bottom edge 26 of the pyramid 32 and the triangular plate 30. The size of the spacers, and thus the size of the gap 28 varies depending on the location of, and the type of plant being emulated. However, a typical range of size might be from about 0.005 inches to about 0.025 inches.

A bolt 36 extends through the apex 38 of the pyramid 32, through an insulating bushing 40 in a hole 42 in the plate 30, and is secured by a nut 44. The tension of the bolt 36 sandwiches the spacers 34 between the pyramid 32 and the plate 30. The emulator 20 can be provided with insulating feet 46. These feet may be secured with screws 48, which can extend into the plate 30.

A coaxial cable 50 has one of its leads 52 connected to the plate 30, and the other of its leads 54 connected to the pyramid 32 (for example via the bolt 36). The cable 50 extends to a monitoring device or computer, represented generally as 56, which monitors conductivity/resistance across the gap 28. When there is no moisture present the conductivity across gap 28 is about 0, and the resistance is nearly $\infty$; when there is moisture present, the conductivity increases to about $5 \times 10^{-7}$ to $2 \times 10^{-6}$ mho, and the resistance drops to about 0.5 to 2MΩ.

While the invention is illustrated with a triangular first surface 22 and a pyramidal second surface 24 with a triangular base, there are a wide variety of suitable configurations. For example the first surface 22 could have some other polygonal shape, and the pyramid could have a base of corresponding shape. Alternatively, instead of a complete pyramid, the second surface could comprise a frustrum of a pyramid. Moreover, the first surface could be circular, and the second surface could be a cone of a frustrum of a cone. There are numerous other suitable configurations and orientations, that could be used so long as an edge of the second surface is spaced by a gap above the first surface.

Moisture can accumulate and form droplets on the second surface 24. Because of the slope, these droplets run off the second surface, onto the first surface, bridging the gap between the edge of the second surface and the first surface. When there are one or more droplets bridging the gap between the plates, the conductivity across the gap increases (from 0 to about $0.5-2 \times 10^{-6}$ mho) and the resistivity across the gap decreases (from ∞ to about 0.5-2MΩ.

A correlation between the detection of water droplets in the gap between the plates and the actual wetness of the leaves to be emulated can be empirically determined. The emulator can be adjusted by varying the size of the gap 28 between the plates. The larger the gap size the larger the droplet needed to bridge the gap, and thus the sooner those effects such as evaporation will reduce the droplet size enough to "reset" the emulator. The emulator can also be adjusted by varying the size of the second surface, the greater the size of the surface, the greater the opportunity for moisture to collect, making the emulator more sensitive to moisture. The emulator can also be adjusted by varying the length of the overlap of the edge of 26 of the second surface over the first plate. The greater the linear compression of the overlapping edge, the greater the chances for one or more droplets to bridge the gap. Finally, the emulator can be adjusted by varying the slope of the second surface. The steeper the slope, the faster that droplets will run down the surface to the edge.

The pyramidal configuration of the preferred embodiment is believed to offer a number of advantages. First there are several different ways of adjusting the sensitivity of the emulator as discussed above. Second the outwardly facing faces of the pyramid each have a different orientation so that at least some of the sides are protected direct sunlight and wind, as would be the case with at least some of the leaves that are being emulated.

OPERATION

In operation the emulator is constructed, and its output is empirically correlated to the actual wetness of the plant leaves that it is emulating, for the particular locale. This can be accomplished by modifying the parameters of the emulator 20 and/or by altering how the signal from the emulator is examined or measured. Once this correlation is established, the emulator 20 can be used to provide a signal corresponding to the wetness of the plants leaves being emulated. When a water droplet bridges the gap 28 between the first and second surfaces, the emulator 20 has a relatively high conductivity and a relatively low resistivity, indicating a wet condition. When there is no water droplet bridging the gap 28 between the first and second surfaces, the emulator has a relatively low conductivity and a relatively high resistivity, indicating a dry condition. The signal can be used as an input for a computer program that forecasts disease infection or propagation as a function of leaf wetness, or as an input for a computer program that forecasts crop condition as a function of leaf wetness.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limited sense.

What is claimed is:

1. A device for providing a signal emulating the wetness of plant leaves, the device comprising: a first generally horizontal surface; a second, generally upwardly facing sloped surface having an edge spaced above the first surface by a gap, so that drops of moisture can accumulate on the second surface, and run off the edge, bridging the gap; and first and second leads extending from the first and second surfaces, respectively, to measure the conductivity/resistivity across the gap.

2. The device according to claim 1 wherein the second surface is generally conical, and wherein the edge of the second surface is generally a circle spaced above the first surface.

3. The device according to claim 1 wherein the second surface is generally pyramidal, and wherein the edge of the second surface is a polygon spaced above the first surface.

4. A method of providing a signal emulating the wetness of plant leaves, the method comprising the steps of:
   providing a first generally horizontal surface;
   providing a second, generally upwardly facing sloped surface having an edge spaced above the first surface by a gap, so that drops of moisture can accumulate on the second surface, and run off the edge, bridging the gap between the first and second surfaces; and measuring the conductivity/resistivity across the gap between the first and second surfaces.

5. The method according to claim 4 wherein the second surface is generally conical, and wherein the edge of the second surface is generally a circle spaced above the first surface.

6. The method according to claim 4 wherein the second surface is generally pyramidal, and wherein the edge of the second surface is a polygon spaced above the first surface.

* * * * *